(12) United States Patent
Orjales Venero et al.

(10) Patent No.: US 6,518,284 B2
(45) Date of Patent: Feb. 11, 2003

(54) 4-SUBSTITUTED PIPERIDINES

(75) Inventors: Aurello Orjales Venero, Neguri (ES); Antonio Toledo Avello, Algorta (ES); Carmen Pumar Duran, Algorta (ES)

(73) Assignee: Faes, Fabrica Espanola de Productos Quimicos Y Farmaceuticos S.A. (ES)

( * ) Notice: Subject to any disclaimer, the term of this patent is extended or adjusted under 35 U.S.C. 154(b) by 0 days.

(21) Appl. No.: 09/824,189

(22) Filed: Apr. 2, 2001

(65) Prior Publication Data

US 2002/0038031 A1 Mar. 28, 2002

Related U.S. Application Data

(63) Continuation-in-part of application No. 09/437,523, filed on Nov. 10, 1999, now abandoned.

(51) Int. Cl.$^7$ .................. A61K 31/4465; C07D 211/12
(52) U.S. Cl. ...................... 514/317; 546/192; 546/236
(58) Field of Search ............................. 546/192, 236; 514/317

(56) References Cited

U.S. PATENT DOCUMENTS 3,634,437 A * 1/1972 Alexander .............. 546/197
4,536,518 A * 8/1985 Welch et al. ............ 514/647

OTHER PUBLICATIONS

English Abstract GB 1203149, Caplus 73:120509 Jun. 10, 1968.*

* cited by examiner

Primary Examiner—Alan L. Rotman
Assistant Examiner—Rita Desai
(74) Attorney, Agent, or Firm—Lackenbach Siegel, LLP

(57) ABSTRACT

New 4-substituted piperidines of the following general formula (I) are disclosed in which $R_1$ and $R_2$ are substituted in unsubstituted aryl radicals, which compounds are obtained as racemic mixtures and as pure enantiomers.

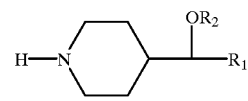

(I)

The compounds, and their pharmaceutically acceptable salts, inhibit the serotonin and/or noradrenaline reuptake, and are useful as medicaments in disorders in which an increase of levels of those neurotransmitters is necessary.

2 Claims, No Drawings

4-SUBSTITUTED PIPERIDINES

This application is a continuation-in-part of U.S. Ser. No. 09/437,523, filed Nov. 10, 1999, now abandoned.

INTRODUCTION

In recent years, selective serotonin reuptake inhibitors (SSRIs) have started to be used for treating depression and other central nervous system disorders, noteworthy among which are fluoxetine, citalopram, sertraline and paroxetine. They all have different chemical structures, which helps to explain their different metabolic and pharmacokinetic profiles.

The present invention relates to a number of new 4-substituted piperidines having an aryloxy functionality and potently inhibiting serotonin and/or noradrenaline reuptake, as a result of their high affinity for their neuronal transporters.

Potential therapeutic applications of these compounds are treatment of nervous bulimia, alcohol addiction, anxiety, obsessive-compulsive disorders, panic, pain, pre-menstrual syndrome and social phobia, as well as migraine prophylaxis. Bibliography also describes other piperidine derivatives with aryloxy functionality as potential antidepressants, albeit with a chemical nature differing essentially from those claimed herein, since the piperidine is substituted at the 3-position. That is for instance the case of such compounds as 3-[(2-methoxyphenoxy)phenyl]methyl-piperidine 1 (Melloni, P., Carniel, G., Della Torre, A., Bonsignalari, A., Buonamici, M., Pozzi, O., Ricciardi, S., Rossi, A. C. *Eur. J. Med. Chem. Chim. Ther.* 1984, 3, 235–242; Melloni, P., Della Torre, A., De Munari, S., Meroni, M., Tonani, R. *Gazetta Chimica Italiana* 1985, 115, 159–163) and 3-[(phenoxy)phenyl]methyl-piperidine 2 (FR 2,010,615 CA73; 66442j; GB 1,203,149 CA73: 120509b). In these compounds, the substitution of the piperidine ring at the 3-position results in an additional chiral centre. The presence of the two chiral centres results in diastereomeric mixtures, which is the form in which the preparation of these compounds

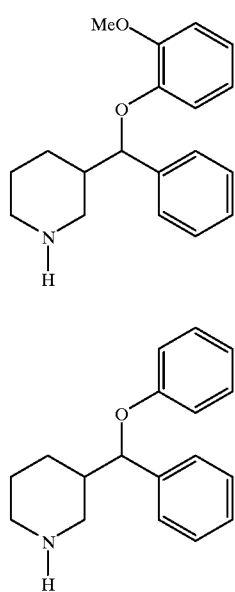

has been described. The preparation and/or isolation of pure enantiomers is not described in any case. However, the compounds claimed in the present specification possess a single chiral centre, since they have the piperidine ring substituted at the 4-position. They have been prepared as racemic mixtures and as pure enantiomers, using synthetic methods differing from those used in preparing 1 and 2.

Moreover, other piperidine derivatives having aryloxy functionality and the piperidine ring substituted at the 4-position have been described as potential antidepressants (formulae 3 and 4). Thus, in the case of 3 type compounds (JP 96 40,999 CA124: 343333n),

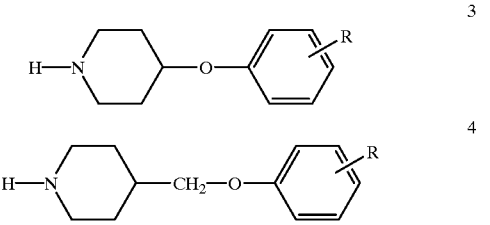

the aryloxy group is directly joined to the piperidine ring, whereas in the 4 type compounds (JP 96 40,999 CA124: 343333n) said group is joined to the piperidine ring through a methylene group which has no further substitutions. The compounds described herein differ largely from those, since they have the aryloxy group joined to the piperidine ring through a methylene group wherein, in all cases, one of the methylene group hydrogens is substituted by an aryl group, substituted or not, as defined hereinafter. These compounds are therefore structurally different from the 3 and 4 types and the synthetic methodology used in preparing the same is also absolutely different.

DESCRIPTION

The new 4-substitude piperidines described in the present invention are represented by general formula (I), in which groups $R_1$ and $R_2$ are non-substituted aryl radicals or aryl radicals mono- or poly-substituted with halogen (fluorine, chlorine, bromine, iodine), alkyl, alkoxy, cyano, trifluoromethoxy, trifluoromethyl, benzoyl, phenyl, nitro, amino, aminoalkyl, aminoaryl and carbonylamino.

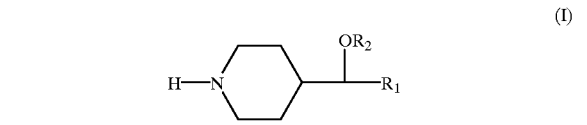

The compounds of general formula (I) have an asymmetric centre and have been prepared as racemic mixtures and as pure enantiomers. The present invention includes all optical isomers of the compounds of general formula (I) and racemic mixtures thereof. The present invention also comprises the pharmaceutically acceptable salts of these compounds with inorganic acids (such as: hydrochloric, hydrobromic, nitric, sulphuric and phosphoric) and with organic acids (such as: acetic, fumaric, tartaric, oxalic, citric, p-toluenesulphonic and methanosulphonic).

The racemic compounds of general formula (I) were prepared using well-known synthetic methods starting with the compounds of general formula (II).

Formation of the alklarylether group was carried out using the Mitsunobu reaction (Mitsunobu, O. *Synthesis* 1981, 1; Hughes, D. L. *Organic Reactions* 42, 335) with phenols $R_2$—OH, in which $R_2$ is an aryl radical, substituted or not, as described for general formula (I), and the compounds of general formula (II), in which $R_1$ is an aryl radical, substituted or not, as described for general formula (I), and $R_3$ is hydrogen or $R_4$, which is an alkoxycarbonyl radical, preferably ethoxycarbonyl and t-butoxycarbonyl.

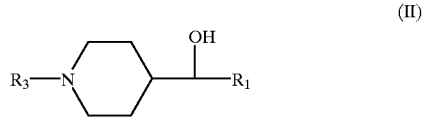
(II)

The alkylarylether group was also prepared using an aromatic nucleophilic substitution reaction (Berglund, R. A. Org. Proc. Res. Dev. 1997 1, 328–330) with the compounds of general formula (II) defined above, and the fluorinated derivatives $R_2$—F, in which $R_2$ is an aryl radical mono- or poly-substituted with halogen (fluorine, chlorine, bromine, iodine), alkyl, alkoxy, cyano, trifluoromethoxy, trifluoromethyl, benzoyl, phenyl, nitro, amino, aminoalkyl, aminoaryl and carbonylamino. The compounds of general formula (II) were prepared using conventional synthetic methods, starting with the compounds of general formula (III) (Duncan, R. L., Helsley, G. C., Welstead, W. J., DaVanzo, J. P., Funderburk, W. H., Lunsford, C. D. J. Med. Chem. 1970, 13 (1), 1), in which $R_5$ is an acetyl radical, ethoxycarbonyl and R6 is cyano or carboxy.

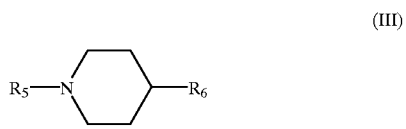
(III)

The compounds of general formula (III) defined above were transformed into the compounds of general formula (IV), in which $R_1$ is an aryl radical, substituted or not,

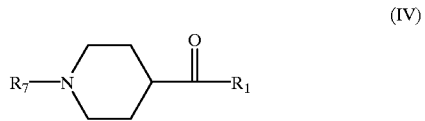
(IV)

as described for the compounds of general formula (I), and $R_7$ is hydrogen, acetyl or $R_4$, which is an alkoxycarbonyl radical, preferably ethoxycarbonyl and t-butoxycarbonyl. Such transformation was made using two reaction types: a) a Friedel-Crafts reaction of the acid chlorides derived from the compounds of general formula (III), in which $R_5$ is an acetyl or ethoxycarbonyl and $R_6$ is carboxy (Duncan, R. L., Helsley, G. C., Welstead, W. J., DaVanzo, J. P., Funderburk, W. H., Lunsford, C. D. J. Med. Chem. 1970, 13 (1), 1) with benzene or conveniently functionalised derivatives thereof; or b) a Grignard reactive addition reaction, prepared from conveniently functionalised aryl halides, to compounds of general formula (III) in which $R_5$ is acetyl, ethoxycarbonyi or t-butoxycarbonyl and $R_6$ is cyano (Duncan, R. L., Helsley, G. C., Welstead, W. J., DaVanzo, J. P., Funderburk, W. H., Lunsford, C. D. J. Med Chem. 1970, 13 (1), 1). Reduction of the compounds of general formula (IV) described provides the general formula (II) alcohols defined above.

The enantiomers composing the racemic mixtures of general formula (I) were obtained using two different pathways: a) resolution of the corresponding racemic mixture by split crystallisation of the diastereomeric salts prepared with chiral acids (D or L-dibenzoyltartaric, D or L-tartaric, D or L-di-p-toluyltartaric and D or L-mandelic) and b) enantioselective synthesis. In the latter case, the enantiomers of general formula (I) were obtained by reacting phenols $R_2$—OH or the fluorinated aromatic derivatives $R_2$—F defined above, with the enantiomers of the general formula (II) alcohols, as described for the racemic mixtures of general formula (I). In the enantiomers of the general formula (II) alcohols, $R_1$ is an aryl radical, substituted or not, as defined for the compounds of general formula (I), and $R_3$ is hydrogen or $R_4$, which is an alkoxycarbonyl radical, preferably ethoxycarbonyl and t-butoxycarbonyl. The enantiomers of the general formula (II) alcohols defined above were obtained by enantioselective reduction (arnachandran, P. V., Teodorovic, A. V., Rangaishenvi, M. V., Brown, H. C. J. Org. Chem. 1992, 57, 2379–2386) of the compounds of general formula (IV) (Duncan, R. L., Helsley, G. C., Welstead, W. J., DaVanzo, J. P., Funderburk, W. H., Lunsford, C. D. J. Med. Chem. 1970, 13 (1), 1), in which $R_1$ is an aryl radical, substituted or not, as defined for the compounds of general formula (I), and $R_7$ is hydrogen or R4, defined above.

The pharmacological activity of the compounds of general formula (I) was determnined-using well-established in vitro and in vivo pharmacological processes. The affinity of the compounds for the serotonin reuptake receptors (5HT) was evaluated in fuill rat cerebral cortex, using P[$^3$H]-paroxetine as radioligand (Habert, E., Graham, D., Tahraoui, L., Claustre, Y., Langer, S. Z. Eur J. Pharmacol. 1985, 118, 107–114) yielding $K_i$ values ranging between 0.5 and 500 nmol/l. The affinity of the compounds for noradrenaline (NA) reuptake receptors was evaluated in full rat cerebral cortex, using [$^3$H]-nisoxetine as radioligand (Tejani-Butt, S. M., J. Pharmacol. Exp. Ther. 1992, 260, 1, 427–436), yielding $K_i$ values ranging between 1 and 500 nmol/l.

The compounds with $K_i$ ranging between 0.5 and 40 nmol/l, for one of the transporters or for both, displayed an excellent antidepressant activity in the three models when administered within the 1 to 30 mg/Kg range orally, intraperitoneally or subcutaneously. See Example 9.

The following examples illustrate the scope of the present invention, which is not howsoever limited to such examples.

EXAMPLE 1

(+/−)-4-[(4-trifluoromethoxyphenoxy)-2-(4-fluorophenyl)]Methyl-piperidine, Fumarate A mixture of (+/−)-4-[(4-trifluoromethoxyphenyl)hydroxy]methyl 1-piperidinecarboxylic acid, 1,1-dimethylethylester (2.25 g, 7.27 mmol), 2-pyridyl-diphenylphosphine (1.90 g, 7.27 mmol) and 1.3 g (7.4 mmol) of 4-trifluoromethoxyphenol in 40 mL of tetrahydrofurane (THF) was treated with a solution of diethyl-azadicarboxylate (DEAD) (1.15 mL) in 10 mL of THF. The reaction mixture was stirred at 20° C. for 4–6 h and concentrated. The residue was dissolved in ethyl ether, washed with an aqueous HCl (10%) solution and an aqueous NaOH (5%) solution, dried (anh. $Na_2SO_4$), filtered-and concentrated. 2.4 g (71%) were obtained of an oil which was dissolved in dichloromethane (50 mL) and treated with a solution of trifluoroacetic acid (2.1 mL) in 10 mL of dichloromethane. After 20 h at 20° C., this was washed with an aqueous NaOH (5%) solution and saturated aqueous NaCl solution. Drying (anh. $Na_2SO_4$), filtering and concentration provided 1.3 g (71%) of the product, which was suspended in anhydrous ether (60 mL) and treated with fumaric acid (0.42 g), yielding 1.0 g of the fumarate (60% yield) with a m.p.,=130–134°C. The RMN-$^1$H (DMSO-$d_6$) displayed a characteristic signal at 4.31 ppm (d, J=5.9 Hz, 1H, CHOAr) and RMN-$^{13}$C (DMSO-$d_6$) displayed at 74.9 ppm a signal corresponding to CHOAr carbon.

EXAMPLE 2

(+/−)-4-[(4-fluorophenoxy)(4-fluorophenyl)]Methyl-piperidine, Hydrochloride

A mixture of (+/−)-4-[(4-fluorophenyl)hydroxy]methyl-1-piperidinecarboxylic acid, 1,1-dimethyl-ethylester (16.33 mmol) and 1.9 g of 4-fluorophenol in 50 mL of THF was treated with 5.0 g of triphenylphosphine and a DEAD solution (3.45 mL) in 10 mL of THF was then added. After 3 h, the solvent was distilled and the resultant oil was treated with hexane, yielding a precipitate which was filtered. The filtrate was concentrated and the residue dissolved in dichloromethane (100 mL) and treated with a trifluoroacetic acid solution (8 mL) in 30 mL of dichloromethane. After 15 h, the reaction was worked as usual and the hydrochloride was prepared in THF, yielding 3.6 g thereof as an amorphous and slightly hygroscopic rose-coloured solid (Yield: 70%) with a m.p. 90° C. (d). RMN-$^1$H (CDCl$_3$) of the hydrochloride displayed a characteristic signal at 4.72 ppm (d, J=5.8 Hz, C$\underline{H}$OAr) and RMN-$^{13}$C (CDCl$_3$) a signal at 83.1 ppm corresponding to $\underline{C}$HOAr carbon.

The following compounds were analogously prepared:

(+/−)-4-[(4-fluorophenoxy)(4-chlorophenyl)]methyl-piperidine, hydrochloride (54% yield, hygroscopic), (+/−)-4-[(4-methoxyphenoxy)(4-fluorophenyl)]methyl-piperidine, fumarate (60% yield, m.p.=139–142° C.), (+/−)-4-(4-trifluoromethylphenoxy)phenyl]methyl-piperidine, hydrochloride (36% yield, hygroscopic), (+/−)-4-[phenoxy)(4-chlorophenyl)]methyl-piperidine, hydrochloride (72% yield, m.p.=80° C. (d)), (+/−)-4-[(4-benzoylphenoxy)phenyl]methyl-piperidine, hydrochloride (74% yield, m.p. 70° C. (d)), and (+/−)-4-[(4-trifluoromethoxy)phenyl]methyl-piperidine, fumarate (58% yield, m.p.=76° C. (d)).

EXAMPLE 3

(+/−)-4-[(4-fluorophenoxy)phenyl]Methyl-piperidine, Sulfate

An NaH (1.95 g, 60% mineral water) suspension in 20 mL of dimethylsulfoxide (DMSO) was treated with a solution of (+/−)-4-(phenylhydroxy)methyl-1-piperidinecarboxylic acid, 1,1-dimethyl-ethylester (13.8 g, 47 mmol) in 36 mL of DMSO. Potassium benzoate (7.5 g, 47 mmol) and 1.4-difluorobenzene (6.1 mL, 56 mmol) were added, and the reaction mixture was heated to 85° C. until the starting substance disappeared. This was then treated with saturated aqueous NaCl and water solution, and extracted with ethyl ester. The organic phase evaporation residue was treated with methanol (200 mL) and aqueous HCl (10%, 200 mL) solution and refluxed for an hour. The product was isolated with the usual methodology, yielding an oil (9.6 g, 72% yield). RMN-$^1$H (CDCl$_3$) displayed a signal at 4.70 ppm (d, J=7.1 Hz, C$\underline{H}$OAr) and RMN-$^{13}$C (CDCl$_3$) a signal at 85.0 ppm corresponding to $\underline{C}$HOAr carbon. The oil was treated with a 1.85 mL conc. H$_2$SO$_4$ solution in 90 mL of water, yielding the sulfate as a solid with a m.p.=118–120° C. (75% yield).

EXAMPLE 4

(+/−)-4-[(3-fluorophenoxy)phenyl]Methyl-piperidine, Sulfate

An NaH (0.40 g, 60% mineral water) suspension in 6 mL DMSO was treated with a solution of (+/−)-4-(phenylhydroxy)methyl-1-piperidinecarboxylic acid, 1,1-dimethyl-ethylester (2.55 g, 8.75 mmol) in 6 mL of DMSO. Potassium benzoate (1.35 g, 8.43 mmol) and 1.3difluorobenzene (1.05 mL, 10.6 mmol) were added, and the reaction mixture was heated to 85° C. until the starting substance disappeared. It was then treated with saturated aqueous NaCl and water solution, and extracted with ethyl ester. The organic phase evaporation residue was treated with methanol (30 mL) and aqueous HCl (10%, 30 mL) solution and refluxed for an hour. The usual reaction working process yielded 2.16 g of an amber oil (88% yield). RMN-$^1$H (CDCl$_3$) displayed a signal at 4.78 ppm (d, J=6.4 Hz, 1H, C$\underline{H}$OAr) and RMN-$^{13}$C (CDCl$_3$) a signal at 84.6 ppm corresponding to $\underline{C}$HOAr carbon. The oil was treated with a 0.20 mL conc. H$_2$SO$_4$ solution in 10 mL of water, yielding the sulfate as a solid with a m.p.=72–76° C.

The following compounds were analogously prepared:

(+/−)-4-(phenoxyphenyl)methyl-piperidine, hydrochloride (73% yield, hygroscopic), (+/−)-4-[(4-cyanophenoxy)phenyl]methyl-piperidine, fumarate (81% yield, m.p.=76° C. (d)), (+/−)-4-[(3-trifluorophenoxy)phenyl]methyl-piperidine, hydrochloride (72% yield, m.p.=58° C. (d)), (+/−)-4-[(4-bromophenoxy)phenyl]methyl-piperidine, sulfate (70% yield, m.p.=99–103° C.), (+/−)-N,N-dimethyl-4-[[(4-piperidinyl)phenyl]methyl]oxy-benzamide, hydrochloride (72% yield, m.p.=45° C. (deliquescent)), (+/−)-4-[(4-nitrophenyloxy)phenyl]methyl-piperidine, hydrochloride (80% yield, m.p.=80° C. (d)), (+/−)-4-[(4-chlorophenyl)(1-naphthyloxy)]methyl-piperidine, sulfate (72% yield, m.p.=186° C. (d)), (+/−)-4-[(1-naphthyloxy)phenyl]methyl-piperidine, sulfate (70% yield, m.p.=152° C. (d)), (+/−)-4-[(2-fluorophenoxy)phenyl]methyl-piperidine, sulfate (72% yield, m.p.=76° C. (d)), (+/−)-4-[(3-cyanophenoxy)phenyl]methyl-piperidine, hydrochloride (80% yield, m.p.=82° C. (d)), (+/−)-4-[(3-chlorophenoxy)phenyl]methyl-piperidine, sulfate (60% yield, m.p.=101–104° C.), (+/−)-4-[(2-trifluoromethylphenoxy)phenyl]methyl-piperidine, sulfate (80% yield, m.p.=110° C. (d)), (+/−)-4-[(2-cyanophenoxy)phenyl]methyl-piperidine, oxalate (80% yield, m.p.=105° C. (d)), (+/−)-4-[[(2-biphenyl)oxy]phenyl]methyl-piperidine, hydrochloride (84% yield, m.p.=84–87° C.), (+/−)-4-[[(4-biphenyl)oxy]phenyl]methyl-piperidine, hydrochloride (82% yield, m.p.=130° C. (d)), (+/−)-4-[(3-bromophenoxy)phenyl]methyl-piperidine, sulfate (75% yield, m.p.=98° C. (d)), (+/−)-4-[(4-iodophenoxy)phenyl]methyl-piperidine, sulfate (57% yield, m.p.=105° C. (d)), (+/−)-4-[(3-iodophenoxy)phenyl]methyl-piperidine, sulfate (37% yield, m.p.=127° C. (d)), (+/−)-4-[(3,5-difluorophenoxy)phenyl]methyl-piperidine, sulfate (86% yield, m.p.=206–208° C.), (+/−)-4-[(3-fluoro-2-methylphenoxy)phenyl]methyl-piperidine, sulfate (80% yield, m.p.=125° C. (d)), (+/−)-4-[(3-chloro-4-cyanophenoxy)phenyl]methyl-piperidine, hydrochloride (70% yield, m.p.=125° C. (d)), (+/−)-4-[(5-chloro-2-methylphenoxy)phenyl]methyl-piperidine, sulfate (75% yield, m.p.=105° C. (d)), (+/−)-4-[(3-chloro-2-methylphenoxy)phenyl]methyl-piperidine, sulfate (89% yield, m.p.=130° C. (d)), (+/−)-4-[(3,4-dichlorophenoxy)phenyl]methyl-piperidine, sulfate (91% yield, m.p.=108° C. (d)), (+/−)-4-[(3-methoxy-5-fluorophenoxy)phenyl]methyl-piperidine, hydrochloride (65% yield, m.p.=200–203° C. (d)), and (+/−)-4-[(3-fluoro-5-cyanophenoxy)phenyl]methyl-piperidine, hydrochloride (76% yield, m.p.=70° C. (d)),

EXAMPLE 5

Resolution of (+/−)-4-[(3-fluorophenoxy)phenyl] Methyl-piperidine 4.45 g of L-(−)-dibenzoyltartaric acid were added over 7.1 g (25 mmol) of (+/−)-4-[3-fluorophenoxy) phenyl]methyl-piperidine dissolved in 175 mL of ethanol (96%). A white solid was obtained (m.p.=212° C. (d)) which was treated with aqueous NaOH (5%) solution and extracted with chloroform, yielding the levorotary isomer (96% ee, m.p.= 59–62° C., $[\alpha]_{546}$−11.4, c =0.576, $CHCl_3$).

The filtrate liquids obtained were concentrated and the free base was extracted by treatment with aqueous NaOH (5%) solution and chloroform. The product obtained, dissolved in ethanol, was treated with D-(+)-dibenzoyltartaric acid using the preceding process. A white solid was obtained (m.p.=208° C. (d)) which was treated with aqueous NaOH (5%) solution and extracted with chloroform, yielding the dextrorotary isomer (98% ee, m.p.=59–62° C., $[\alpha]_{546}$+11.4, c=0.618, $CHCl_3$).

The following compounds were analogously prepared:

(+)-4-[(4-fluorophenoxy)phenyl]methyl-piperidine (96% ee, m.p.=100–102° C., $[\alpha]_{546}$+14, c=0.259, $CHCl_3$)

(−)-4-[(4-fluorophenoxy)phenyl]methyl-piperidine (96% ee, m.p.=100–102° C., $[\alpha]_{546}$−14, c=0.237, $CHCl_3$)

(+)-4-[(4-trifluoromethylphenoxy)phenyl]methyl-piperidine, sulfate (96% ee, m.p.=85° C. (d), $[\alpha]_{365}$+17.8, c=0.556, $CHCl_3$)

(−)-4-[(4-trifluoromethylphenoxy)phenyl]methyl-piperidine, sulfate (96% ee, m.p.=85° C. (d), $[\alpha]_{365}$−15.5, c=0.508, $CHCl_3$)

(+)-4-[(4-bromophenoxy)phenyl]methyl-piperidine (96% ee, m.p.=129–131° C. (d), $[\alpha]_{436}$+54, c=1.012, $CHCl_3$)

(−)-4-[(4-bromophenoxy)phenyl]methyl-piperidine (95% ee, m.p. 129–131° C. (d), $[\alpha]_{436}$−54.1, c =1.048, $CHCl_3$)

(+)-4-(3-chlorophenoxy)phenyl]methyl-piperidine, methanosulfate (98% ee, m.p.=200–202° C. (d), $[\alpha]_{365}$+14.6, c=0.646, $CHCl_3$)

(−)-4-[(3-chlorophenoxy)phenyl]methyl-piperidine, methanosulfate (99% ee, m.p.=200–202° C. (d), $[\alpha]_{365}$+13.6, c=0.690, $CHCl_3$)

(+)-4-[(3-cyanophenoxy)phenyl]methyl-piperidine, hydrochloride (95% ee, m.p.=70° C. (d), $[\alpha]_{436}$+26.5, c=0.600, $CHCl_3$)

(−)-4-[(3-cyanophenoxy)phenyl]methyl-piperidine, hydrochloride (98% ee, m.p.=70° C. (d), $[\alpha]_{365}$−27.1, c=0.680, $CHCl_3$)

(+)-4-[(3,5-difluorophenoxy)phenyl]methyl-piperidine, sulfate (96% ee, m.p.=78° C. (d), $[\alpha]_{436}$+19.4, c=0.80, CHC]3)

(−)-4-[(3,5-difluorophenoxy)phenyl]methyl-piperidine, sulfate (98% ee, m.p.=78° C. (d), $[\alpha]_{436}$−19.8, c=0.724, $CHCl_3$)

(+)-4-[(3-fluorophenoxy)(3-fluorophenyl)]methyl-piperidine, hydrochloride (96% ee, m.p.=75° C. (d), $[\alpha]_{546}$+15, c=0.183, $CHCl_3$) and (−)-4-[(3-fluorophenoxy)(3-fluorophenyl)]methyl-piperidine, hydrochloride (95.4% ee, m.p.=78° C. (d), $[\alpha]_{546}$−16, c=0.17, $CHCl_3$)

EXAMPLE 6

(+)-4-[(4-fluorophenoxy)phenyl]Methyl-piperidine 4-benzoyl-piperidine (2.0 g, 10.6 mmol) was added over a solution of 6.8 g of (+)-B-chlorodiisopinocanfeilboran ((+)-DIP-Cl) (21.25 mmol) in dichloromethane (20 mL, dry) cooled down to 3–4° C. After reacting for 72 h, 2.0 mL of acetaldehyde (35.46 mmol) were added and stirred at room temperature for 3 h. 24 mL of an aqueous NaOH (6N) solution, dichloromethane and saturated aqueous NaCl solution were added. The phases were separated and the usual treatment of the organic phase provided (+)-α-phenyl4-piperidinemethanol as a white solid with a m.p.=64–66° C. in a 90% yield (84% ee).

1.8 g of aminoalcohol (+)-α-phenyl-4-piperidinemethanol (9.6 mmol) were dissolved in methanol (10 mL). The solution was cooled down to 0° C. and a diterbutyl dicarbonate $((Boc)_2O)$ (2.5 g, 11.27 mmol) solution was added dropwise to 10 mL of methanol. The mixture was stirred for 24 h at room temperature, the methanol was concentrated, water was added and extracted with dichloromethane. The usual treatment of the organic phase provided the desired alcohol as a slightly coloured oil in a 93% yield.

The alcohol prepared above (2.7 g, 9.3 mmol) dissolved in DMSO (25 mL) was added over an NaH (60%, 0.6 g) suspension in DMSO (5 mL). Potassium benzoate (1.53 g, 9.63 mmol) and 1,4-difluorobenzene (1.3 mL, 11.9 mmol) were added and the mixture was heated (70–75° C.) until the starting substance disappeared. The reaction mixture was poured into water and saturated aqueous NaCl solution, and extracted with ether. The oil obtained was refluxed with a mixture of methanol (40 mL) and an aqueous hydrochloric acid (40 mL) solution for 1 h. Isolation of the product using the customary methodology provided (+)-4-[(4-fluorophenoxy)phenyl]methyl-piperidine as an oil in a 54% yield. Treatment of 0.5 g (1.75 mmol) of this oil with D-dibenzoyltartaric acid in ethanol (96%, 30 mL) provided a precipitate which was filtered (m.p.=198–199° C.). The aminoether was released yielding a white solid with a 96% ee, m.p.=102–104° C., and $[\alpha]_{546}$+15, c=0.105, $CHCl_3$).

The following compounds were analogously prepared:

(+)-4-[(4-nitrophenoxy)phenyl]methyl-piperidine, hydrochloride (96% ee, m.p.=55° C. (d), $[\alpha]_{436}$+36, c=0.045, Ethanol)

(−)-4-[(1-naphthyloxy)phenyl]methyl-piperidine, hydrochloride (98% ee, m.p.=65° C. (d), $[\alpha]_{546}$−180, c=0.080, $CHCl_3$) and (+)-4-[(2-fluorophenoxy)phenyl]methyl-piperidine, sulfate (97.6% ee, m.p.=105° C. (d), $[\alpha]_{546}$+31, c=0.081, $CHCl_3$).

EXAMPLE 7

(−)-4-[(4-fluorophenoxy)phenyl]Methyl-piperidine 4-benzoyl-piperidine (7.35 g, 39.05 mmol) was added over a solution of 25 g of (−)-DIP-Cl (78.125 mmol) in dichloromethane (75 mL, dry) cooled down to 0–2° C. After reacting for 72 h, 5.2 mL of acetaldehyde (92.2 mmol) were added and stirred at room temperature for 3 h. 71 mL of an aqueous NaOH (6N) solution, dichloromethane and saturated aqueous NaCl solution were added. The phases were separated and the usual treatment of the organic phase provided (−)-α-phenyl-4-piperidinemethanol as a white solid with a m.p.=48–50° C. in a 85% yield (86% ee).

2 g of aminoalcohol (−)α-phenyl4-piperidinemethanol (10.7 mmol) were dissolved in methanol (10 mL). The solution was cooled down to 0° C. and a $(Boc)_2O$ (2.6 g, 11.73 mmol) solution was added dropwise to 7 mL of methanol. The mixture was stirred for 20 h at room temperature, the methanol was concentrated, water was added and extracted with dichloromethane. The usual treatment of the organic phase provided the desired alcohol as a slightly coloured oil in a 90% yield.

The alcohol prepared above (1.3 g, 4.5 mmol) dissolved in DMSO (10 mL) was added over an NaH (60%, 210 g) suspension in DMSO (5 mL). Potassium benzoate (715 g, 4.5 mmol) and 1,4-difluorobenzene (0.75 mL, 6.86 mmol) were added and the mixture heated (70–75° C.) until the starting substance disappeared. The reaction mixture was poured into water and saturated aqueous NaCl solution, and extracted with ether. The oil obtained was refluxed with a mixture of methanol (17 mL) and an aqueous hydrochloric acid (17 mL) solution for 1 h. The usual working of the reaction provided (−)-4-[(4-fluorophenoxy)phenyl]methyl-piperidine as an oil in a 64% yield. Treatment of this oil with L-dibenzoyltartaric acid in ethanol (96%, 35 mL) provided a precipitate which was filtered (m.p.=193–194° C.). The aminoether was released yielding a white solid with a 98% ee, m.p.=100–102° C., and $[α]_{546}$–14, c=0.2, $CHCl_3$).

The following compounds were analogously prepared:

(−)-4-[(4-nitrophenoxy)phenyl]methyl-piperidine, hydrochloride (98.7% ee, m.p.=59° C. (d), $[α]_{436}$–31, c=0.042, Ethanol)

(+)-4-[(1-naphthyloxy)phenyl]methyl-piperidine, hydrochloride (94% ee, m.p.=115° C. (d), $[α]_{546}$–+156,c=0.128, $CHCl_3$) and (−)-4-[(2-fluorophenoxy)phenyl]methyl-piperidine, sulfate (97.6% ee, m.p.=90° C. (d), $[α]_{546}$–31, c=0.140, $CHCl_3$).

EXAMPLE 8

(+/−)-4-[(3-fluorophenoxy)(3-fluorophenyl)]Methyl-piperidine, Sulfate a mixture of 4-cyanopiperidine (5 g, 40.92 mmol), $(Boc)_2O$ (11.7 g, 53.7 mmol), sodium bicarbonate (11.7 g, 139.3 mmol) and water (117 mL) was stirred at room temperature for 17 h. this was extracted with dichloromethane and the organic phase dried (anh. $Na_2SO_4$), filtered and concentrated. The resultant oil was purified by flash chromatography (Still, W. C., Kahn, M., Mitra, A. *J. Org. Chem.* 1978, 43, 2923) yielding 4-cyano-1-piperidinecarboxylic acid, 1,1-dimethyl-ethylester as a yellow oil in a 43% yield.

A Mg (0.5 g) suspension in ether (dry, 22 mL) was treated with some milliliters (approximately ¼ of the total) of a 1-bromo-3-fluorobenzene (2.15 mL, 19.4 mmol) solution in ether (dry, 16 mL) and an iodine crystal. This was heated until a smooth reflux was observed and the colour disappeared. The rest of the solution was then added dropwise maintaining a mild reflux. With the addition at an end, this was refluxed for 1 h 30 min and allowed to cool down to room temperature. A 4-cyano-1-piperidinecarboxylic acid, 1,1-dimethyl-ethylester (2.7 g, 12.84 mmol) solution was added dropwise to dry ether (27 mL) and the resultant mixture refluxed for 3 h. A saturated aqueous $NH_4Cl$ (50 mL) solution was added and extracted with ether. The usual treatment of the organic phase provided an oil which was purified by flash chromatography (Still, W. C., Kahn, M., Mitra, A. *J. Org. Chem.* 1978, 43, 2923) yielding 2.4 g (61% yield) of 4(3-fluorobenzoyl)-1-piperidinecarboxylic acid, 1,1-dimethyl-ethylester as ayellowish oil.

The product obtained above (2.4 g, 7.8 mmol) was dissolved in methanol (30 mL) and $NaBH_4$(0.2 g) dissolved in 3.5 mL water was added. The mixture was heated for 2 h in an oil bath (50–60° C.) and the product isolated in the usual manner, yielding (+/−)-4-(3-fluorophenyl)hydroxy] methyl-1-piperidinecarboxylic acid, 1,1-dimethyl-ethylester as a very dense yellowish oil in quantitative yield.

A solution of the racemic alcohol prepared above (2.4 g, 7.8 mmol) in DMSO (25 mL) was added dropwise to an NaH (60%) (0.62 g) suspension in DMSO (15 mL). Potassium benzoate (1.53 g, 9.55 mmol) and 1,3-difluorobenzene (1.2 mL, 11.9 mmol) were added and the mixture was heated in an oil bath (65–70° C.) until the starting substance disappeared. This was then poured into a mixture of saturated NaCl (50 mL) solution and water (39 mL). This was extracted with ether and the usual treatment of the ethereal phase provided an oil which was refluxed with a mixture of methanol (40 mL) and aqueous HCl (10 %, 40 mL) solution for 1 h 30 min. The desired product (+/−)-4-[(3-fluorophenoxy)(3-fluorophenyl)]methyl-piperidine was obtained as an amber oil in a 50% yield. RMN-$^1$H ($CDCl_3$) of this product displayed a signal at 4.55 ppm (d, J=6.1 Hz, CHOAr) and RMN-$^{13}$C ($CDCl_3$) a signal at 83.9 ppm corresponding to CHOAr carbon. The oil prepared above was treated with a 0.22 mL conc. $H_2SO_4$ solution in 16.5 mL of water, yielding the sulfate as a slightly coloured solid (m.p.=158° C. (d)).

The following compounds were analogously prepared:

(+/−)-4-[(2-fluorophenoxy)(3-fluorophenyl)]methyl-piperidine, hydrochloride (62% yield, m.p.=90° C.) and (+/−)-4-[(4-fluorophenoxy)(3-fluorophenyt)]methyl-piperidine, hydrochloride (30% yield, m.p.=65° C.).

EXAMPLE 9

The following Table 1, demonstrates the serotonin and noradrenaline reuptake inhibitory activity of the compounds of the present invention. Table 2 discloses the structures of the respective compounds referred to in Table 1.

TABLE 1

| | $K_1$ values (nM) Uptake sites (transporters). Rat brain | | |
|---|---|---|---|
| Compound | Serotonin | Noradrenaline | Dopamine |
| F-97814-TA | 0.45 | 111.44 | 821.04 |
| F-97815-TA | 45.87 | 1451.31 | 253.42 |
| F-98212-TA | 7.29 | 107.39 | >1 μM |
| F-98214-TA | 1.95 | 13.51 | 461.28 |
| F-98404-TA | 14.92 | >10 μM | >1 μM |
| F-98408-TA | 34.77 | >10 μM | >1 μM |
| F-98616-TA | 3.00 | 55.77 | >1 μM |
| F-98620-TA | 1.50 | 44.04 | >1 μM |
| F-98715-TA | 1.68 | 86.90 | 110.5 |
| F-98716-TA | 1.43 | 179.88 | >1 μM |
| F-98814-TA | 1.40 | 24.85 | >1 μM |
| F-98822-TA | 7.09 | 385.9 | >1 μM |
| F-98603-PD | 0.63 | >1 μM | >10 μM |
| F-98610-PD | 15.06 | >1 μM | >1 μM |
| F-98607-PD | 4.20 | 22.51 | >1 μM |
| F-98718-PD | 28.52 | 41.45 | 520.30 |
| F-98828-PD | 9.99 | 127.80 | 112.80 |
| F-98829-PD | 2.83 | 17.47 | >1 μM |
| F-98925-PD | 27.58 | 48.09 | 376.70 |
| F-98917-PD | 4.3 | 19.11 | >1 μM |

TABLE 2
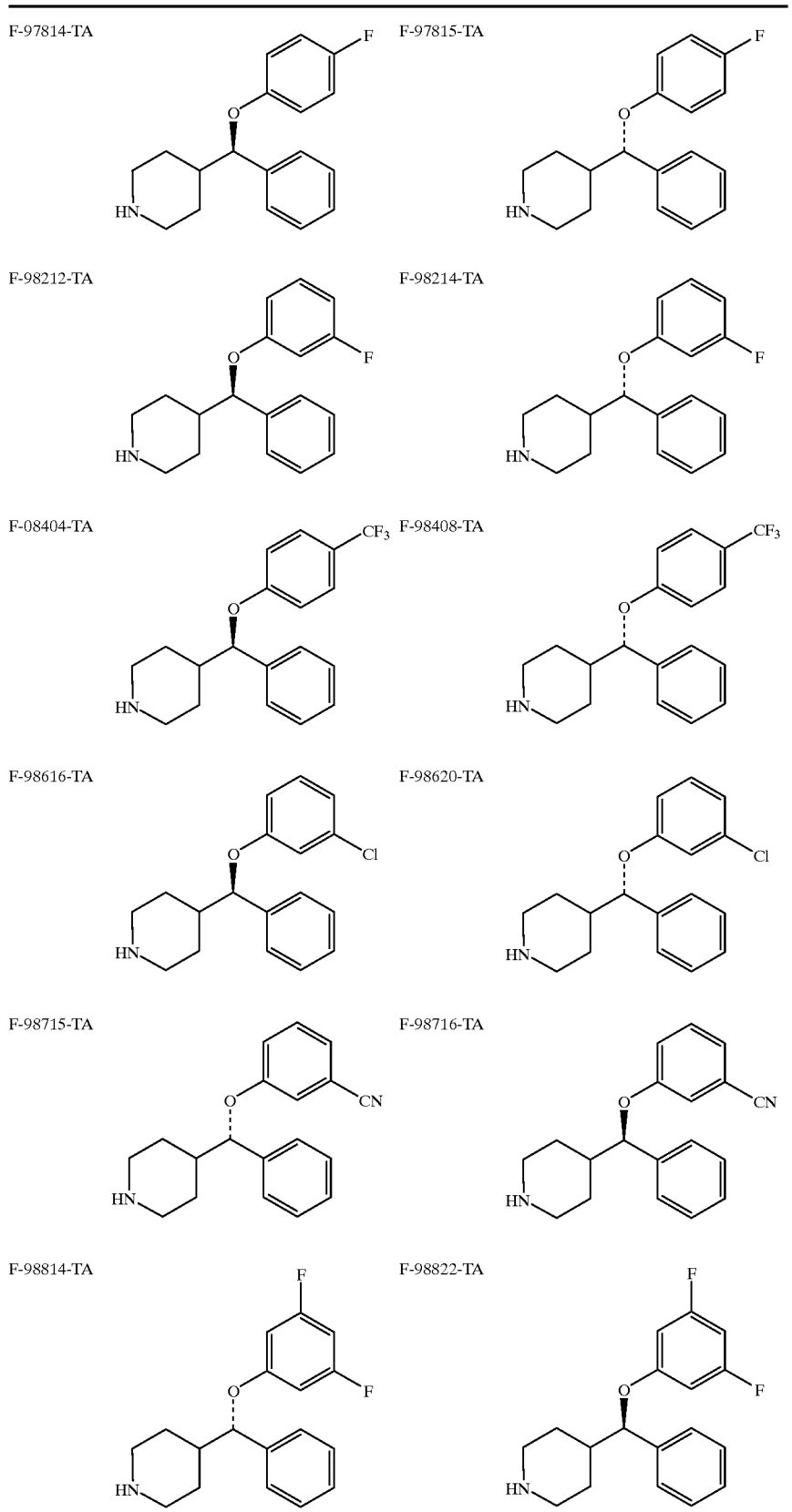

TABLE 2-continued

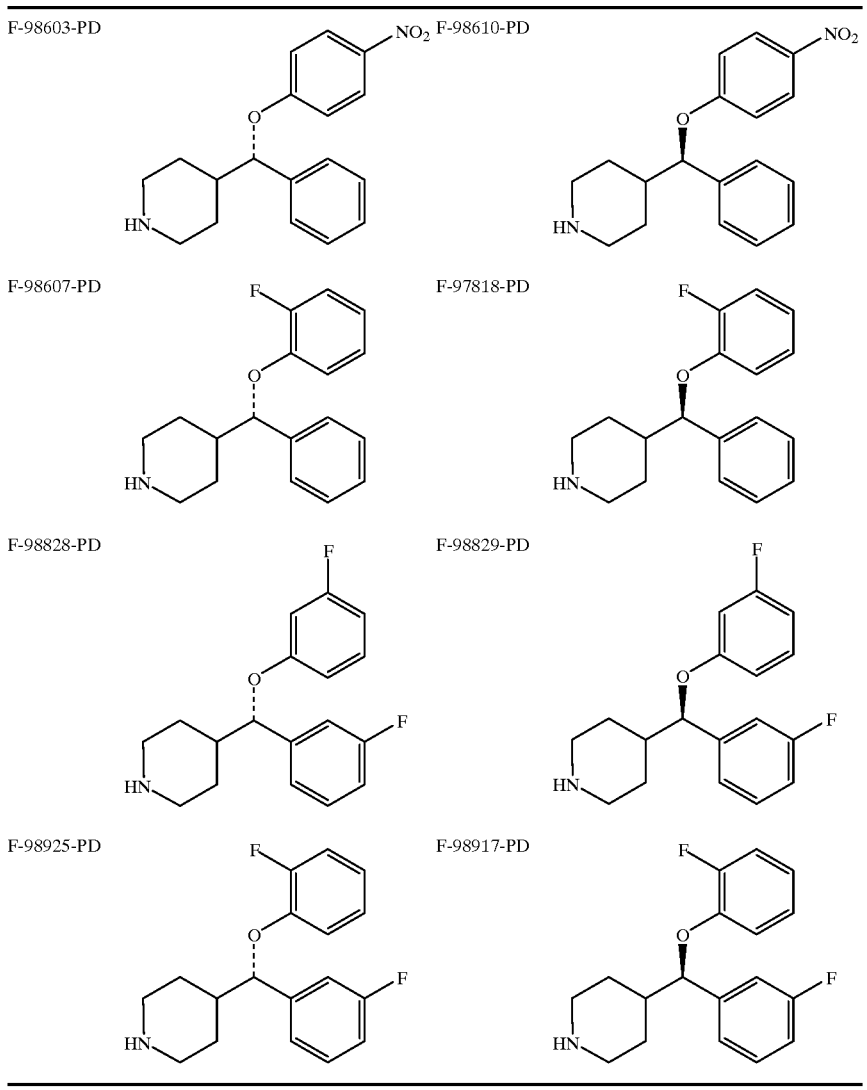

What is claimed is:

1. A method for treating depression in a human by noradrenaline reuptake blocking, in a human in need of such treatment, by administering 1 to 30 mg/Kg of a compound or pharmaceutically acceptable salts thereof having the formula:

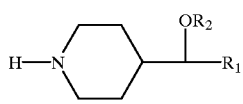

(I)

wherein $R_1$ and $R_2$ are selected from the group consisting of: aryl radicals, and mono-and poly-substituted aryl radicals substituted with one substitutent selected from the group consisting of: halogen, alkyl, alkoxy, cyano, trifluoromethyl, benzoyl, phenyl, nitro, amino, aminoalkyl, aminoaryl, and carbonylamino; and wherein the compound has a $K_i$ for noradrenaline re-uptake transporters between at least 1 and 40 nmol/l.

2. The method of claim 1, wherein the compound is one selected from the group consisting of:

4-[(4-fluorophenoxy)phenyl]metlhyl-piperidine;
4-[(4-methoxyphenoxy)(4-fluorophenyl)]methyl-piperidine;
4-[(4-fluorophenoxy)(4-fluorophenyl)]methyl-piperidine;
4-[(4-fluorophenoxy)(4-chlorophenyl)]methyl-piperidine;
4-[(4-trifluoromethylphenoxy)phenyl]methyl-piperidine;
4-[(4-trifluoromethoxyphenoxy)(4-fluorophenyl)]methyl-piperidine;
4-[phenoxy(4-chlorophenyl)]methyl-piperidine;
4-[(4-benzoylphenoxy)phenyl)]methyl-piperidine;
4-[(4-trifluoromethoxyphenoxy)phenyl]methyl-piperidine;
4-[(4-cyanophenoxy)phenyl]methyl-piperidine;
4-[(3-trifluorophenoxy)phenyl]methyl-piperidine;
4-[(3-fluorophenoxy)phenyl]methyl-piperidine;
4-[(4-bromophenoxy)phenyl]methyl-piperidine;
N,N-dimethyl-4-[[(4-piperidinyl)phenyl]methyl]oxy-benzamide;
4-[(4-nitrophenyloxy)phenyl]methyl-piperidine;

4-[(4chlorophenyl)(1-naphthyloxy)]methyl-piperidine;
4-[(1-naphthyloxyphenyl]methyl-piperidine;
4-[(2-fluorophenoxy)phenyl]methyl-piperidine;
4-[(3-cyanophenoxy)phenyl]methyl-piperidine;
4-[(3-chlorophenoxy)phenyl]methyl-piperidine;
4-[(2-trifluoromethylphenoxy)phenyl]methyl-piperidine;
4-[(2-cyanophenoxy)phenyl]methyl-piperidine;
4-[[(2-biphenyl)oxy]phenyl]methyl-piperidine;
4-[(3-fluorophenoxy)(3-fluorophenyl)]methyl-piperidine;
4-[(2-fluorophenoxy)(3-fluorophenyl)]methyl-piperidine;
4-[(4-fluorophenoxy)(3-fluorophenyl)]methyl-piperidine;
4-[[(4-biphenyl)oxy]phenyl]methyl-piperidine;
4-[(3-bromophenoxy)phenyl]methyl-piperidine;
4-[(4-iodophenoxy)phenyl]methyl-piperidine;
4-[(3-iodophenoxy)phenyl]methyl-piperidine;
4-[(3,5-difluorophenoxy)phenyl]methyl-piperidine;
4-[(3-fluoro-2-methylphenoxy)phenyl]methyl-piperidine;
4-[(3-chloro-4-cyanophenoxy)phenyl]methyl-piperidine;
4-[(5-chloro-2-methylphenoxy)phenyl]methyl-piperidine;
4-[(3-chloro-2-methylphenoxy)phenyl]methyl-piperidine;
4-[(3,4-dichlorophenoxy)phenyl]methyl-piperidine;
4-[(3-methoxy-5-fluorophenoxy)phenyl]methyl-piperidine; and
4-[(3-fluoro-5-cyanophenoxy)phenyl]methyl-piperidine.

* * * * *